(12) United States Patent
Lin et al.

(10) Patent No.: US 6,379,453 B1
(45) Date of Patent: Apr. 30, 2002

(54) PROCESS FOR PRODUCING FAST-SETTING, BIORESORBABLE CALCIUM PHOSPHATE CEMENTS

(75) Inventors: Jiin-Huey Chern Lin, Kaohsiung; Chien-Ping Ju, Room 607, No. 350, Tung Feng Rd., Tainan; Wen-Cheng Chen, Tainan Hsien, all of (TW)

(73) Assignees: Jiin-Huey Chern, Tainan; Chien-Ping Ju, Kaohsiung, both of (TW)

( * ) Notice: Subject to any disclaimer, the term of this patent is extended or adjusted under 35 U.S.C. 154(b) by 0 days.

(21) Appl. No.: 09/351,912

(22) Filed: Jul. 14, 1999

(51) Int. Cl.[7] ............................................... C04B 12/02
(52) U.S. Cl. ........................ 106/690; 106/35; 106/691
(58) Field of Search ........................ 106/35, 690, 691; 423/308

(56) References Cited

U.S. PATENT DOCUMENTS

| | | | |
|---|---|---|---|
| 5,053,212 A | 10/1991 | Constanz et al. | 423/305 |
| 5,092,888 A | 3/1992 | Iwamoto et al. | 623/16 |
| 5,149,368 A | 9/1992 | Liu et al. | 424/602 |
| 5,180,426 A | 1/1993 | Sumita | 106/35 |
| 5,262,166 A | 11/1993 | Liu et al. | 424/423 |
| 5,336,264 A | 8/1994 | Constanz et al. | 623/16 |
| 5,342,441 A | 8/1994 | Mandai et al. | 103/35 |
| 5,503,164 A | 4/1996 | Friedman | 128/898 |
| 5,522,893 A * | 6/1996 | Chow et al. | 423/308 |
| 5,525,148 A | 6/1996 | Chow et al. | 106/35 |
| 5,542,973 A | 8/1996 | Chow et al. | 106/35 |
| 5,545,254 A | 8/1996 | Chow et al. | 106/35 |
| 5,695,729 A | 12/1997 | Chow et al. | 423/305 |
| 5,782,971 A * | 7/1998 | Constantz et al. | 423/308 |
| 5,814,681 A | 9/1998 | Hino et al. | 523/113 |
| 5,820,632 A | 10/1998 | Constanz et al. | 623/16 |
| 5,997,624 A * | 12/1999 | Chow et al. | 106/690 |
| 6,110,851 A * | 8/2000 | Wiedemann | 106/35 |

* cited by examiner

Primary Examiner—Wayne Langel
(74) Attorney, Agent, or Firm—Bacon & Thomas (57) ABSTRACT

A process for producing a fast-setting, bioresorbable calcium phosphate cement. The process of the invention includes a pre-heat treatment step to generate uniformly distributed submicron-sized apatite seed crystals.

7 Claims, 9 Drawing Sheets

PROCESS FOR PRODUCING FAST-SETTING, BIORESORBABLE CALCIUM PHOSPHATE CEMENTS

FIELD OF THE INVENTION

The present invention relates to a process for producing fast-setting, bioresorbable calcium phosphate cements (CPC), and in particular, to a process including a pre-heat treatment step to generate uniformly distributed submicron-sized apatite seeds.

DESCRIPTION OF THE RELATED ART

Due to its superior biocompatibility and osteoconductivity, CPC has been used as implant or filling material in dental or bone prosthesis and the like (Chow et al., 1991;Chohayeb et al., 1987: Costantine et al., 1991j; Firedman et al; Hong et al; 1991; Sugawara et al., 1992; Hamanish et al; 1996). In 1983, Brown and Chow indicated that mixing tetracalcium phosphate (TTCP) and dicalcium phosphate anhydrous (monetite) (DCPA) powder to obtain a powder mixture and mixing the powder mixture in a diluted phosphate-containing solution can obtain hydroxyapatite (HA). Implants made from thus produced HA have a compressive strength up to 51 MPa. However, in application, the setting time is too long (for example, 30 minutes) and the mechanical properties are still inferior compared to enamel, tooth and metal composite. Moreover, as the setting time is long, the material can be flushed away by body fluid/blood before it is set.

A great deal of effort has been expended to solve the long setting time problems. U.S. Pat. No. 4,959,104 provides a process for producing a fast-setting CPC which becomes set within several minutes. Inorganic fluorides, such as $CaF_2$, $MgF_2$ and $BeF_2$ are added to increase the compressive strength of the CPC. NaF, LiF or KF is added in the organic acid or inorganic acid solution to shorten the setting time to form a stable apatite type product.

U.S. Pat. No. 5,092,888 provides a hardening material comprising (1) a powder component composed of a powdery mixture of tetracalcium phosphate and calcium phosphate having a Ca/P atomic ratio lower than 1.67 and (2) a liquid component composed of a colloidal aqueous solution comprising solid colloid particles dispersed in an aqueous medium.

U.S. Pat. No. 5,180,426 provides a calcium phosphate type setting material comprising (1) powder comprising at least one of α-tricalcium phosphate and tetracalcium phosphate; and (2) a setting solution comprising an aqueous acidic solution having dissolved therein at least one polysaccharide selected from the group consisting of carboxymethyl chitin, glycol chitin, pullalan, high methoxy-pectin and chitosan.

U.S. Pat. No. 5,262,166 provides a surgical cement comprising a calcium alkali phosphate cement with relatively high surface pH of about 7 or higher. In the calcium alkali phosphate cement, citric acid, acidic citrate salts are added as setting agent and CaO, $Na_2O$, $P_2O_5$, MgO and collagen are added to shorten the setting time.

U.S. Pat. Nos. 5,336,264 and 5,820,632 show that setting times of calcium phosphate cement compositions are enhanced by the addition of sodium phosphate or sodium carbonate lubricant compositions.

U.S. Pat. No. 5,525,148 provides a composition relating to calcium phosphate cement that self-hardens substantially to hydroxyapatite at ambient temperature when in contact with an aqueous medium. Phosphates such as $Na_3PO_4$, $Na_2HPO_4$ and $NaH_2PO_4$ are added in the composition.

As discussed above, these approaches use metal ion-containing compounds, polymeric compounds or collagens as the setting agents to improve the long setting time problem. Metal ions in setting agents may cause diseases when applied in vivo. Some evidence shows that aluminum ions might be associated with peripheral neuropathy, osteomalacia and aizheimer diseases; vanadium ions can cause cytotoxicity; Ni and Cr compounds may cause cancer; and Ni or Cr metal ions can induce the immunological sensitization of human beings. Although titanium and titanium alloys are considered bio-compatible, it was recently reported that scraps of titanium alloys may also cause detrimental reactions to the vicinal living tissues or cause cytotoxicity (K. Soballe, "Hydroxyapatite ceramic coating for bone implant fixation", ACTA Orthopaed. Scandin Supplem., 64:1–58, 1993; J. J. Callaghan, Current concerts review, "The clinical results and basic science of total hip arthroplasty with porous-coated prostheres" J. Bone Joint Surg., 75A: 299–310, 1993). Polymeric compounds may degrade into their monomers which are also detrimental biologically. While collagens are biocompatible, their dissolution rates are usually too high and found practically inconvenient.

Bioresorbable materials have advantages when being used in medical implants. Bioresorbable materials will be gradually degraded when they are implanted in animals or humans, thus allowing replacement by new bone growth.

U.S. Pat. No. 5,053,212 discloses the production of a bioresorbable hydroxyapatite. A dry mixture is first provided in which TTCP and ortho-phosphoric crystals, monocalcium phosphate monohydrate are combined with mechanical mixing to control the Ca/P ratio to approximately 1.25–2.0:1. The dry mixture is then mixed with water or polyols or ethylene glycol to obtain the bioresorbable hydroxyapatite.

U.S. Pat. No. 5,149,368 provides a process for the preparation of bioresorbable calcium phosphate cement. The process uses decomposable tricalcium phosphate and tetra-calcuim phosphate as main ingredients and undecomposable hydroxyapatite as secondary ingredients. These ingredients are intensively mixed with setting agents, i.e., acidic citrate, to obtain a mixture and the mixture is then mixed with an appropriate solvent to obtain a slurry. NaOH, KOH or $NH_4OH$ is added to adjust the pH to greater than 5. Antibiotics and bone morphological proteins are also added. The resultant calcium phosphate cements are biocompatible, bioresorbable and have satisfactory working time.

U.S. Pat. No. 5,342,441 provides a biocompatible composition which includes a powder component containing $Ca_4P_2O_9$ and at least one of $CaHPO_4$ and $CaHPO_4H_2O$ at a molar ratio of Ca:P of 1.16–1.95; and a liquid component containing 1 mM to 2M of a second phosphate ion and 1 mM to 2M of an organic ion. The biocompatible material converts into hydroxyapatite when being implanted into human or animals and a part thereof can be replaced by newly grown bones.

U.S. Pat. No. 5,503,164 provides a method for the repair of craniomaxillofacial bony defects using a low temperature-hardening, gradually resorbable hydroxyapatite forming cement. The resorbable hydroxyapatite forming cement is obtained by adding some bio-dissolvable salts such as silicate acrylic salts.

U.S. Pat. Nos. 5,542,973, 5,545,254 and 5,695,729 provide a composition comprising tetracalcium phosphate which has been prepared from a mixture with a calcium to phosphorous ratio of less than 2 under substantially anhydrous or vacuum conditions and which is converted substantially to hydroxyapatite upon setting.

U.S. Pat. No. 5,814,681 provides a restorative composition for hard tissue, comprising a paste (A) containing an inorganic calcium phosphate powder, a polymerizable monomer mixture and a polymerization initiator, and a paste (B) containing an inorganic calcium phosphate powder, a polymerizable monomer mixture and a polymerization accelerator.

However, these processes for producing biodegradable compositions use expensive additives or require a complicated procedure, such as being conducted in a vacuum or a water-free ambient.

SUMMARY OF THE INVENTION

It is therefore an object of the invention to provide simple, inexpensive and easy to control process for producing a fast-setting biocompatible, bioresorbable calcium phosphate cement.

The invention accomplishes the above object by providing a process comprising the following steps: obtaining a powder mixture from at least one calcium phosphate selected from the group consisting of $Ca_4(PO_4)_2O$, $CaHPO_4$ $2H_2O$, $CaHPO_4$, $Ca_8H_2(PO_4)_6$ $5H_2O$, $\alpha$-$Ca_3(PO_4)_2$, $\beta$-$Ca_3(PO_4)_2$, $Ca_2P_2O_7$, $Ca_2H_2P_2O_8$, wherein the molar ratio of Ca to P in the mixture is roughly between 1 and 2; mixing the powder mixture in a phosphate-containing solution to obtain a powder/solution mixture having a concentration of less than 4 g powder mixture per 1 ml solution; immediately heating the powder/solution mixture to a temperature of roughly 50° C.–350° C. to obtain a powder containing uniformly distributed submicron-sized apatite crystals; and mixing the apatite crystal-containing powder in a phosphate ion-containing solution to obtain a fast-setting, bioresorbable calcium phosphate cement.

The process can further include adding approximately 3% by weight of additional phosphate or fluoride-containing compounds to the phosphate ion-containing solution in the step of mixing the apatite crystal-containing powder in a phosphate ion-containing solution to increase the bioactivity of the resulting CPC.

The present invention also provides a fast-setting, bioresorbable calcium phosphate cement prepared by the above described process. In addition, the present invention provides a composite comprising a fast-setting, bioresorbable calcium phosphate cement prepared by the above described process and at least one other bioresorbable powder, for example calcium phosphate powder or bioactive glass powder. The composite can either be in the form of a matrix of CPC into which the bioresorbable powder is interspersed or alternating layers of CPC and bioresorbable powder.

The process of this invention is simple and the parameters are easy to control. By using a pre-heat treatment to generate apatite seeds, the seeds are more uniformly distributed than when externally added because powder aggregation can be avoided, and seed size can be easily controlled to meet different applications. Furthermore, the internally nucleated seeds are more biocompatible than other added seeds (for example, $Al_2O_3$), and can be easily combined with calcium phosphate, collagens, and bioresorbable polymer. dr

BRIEF DESCRIPTION OF THE DRAWINGS

The following detailed description, given by way of examples and not intended to limit the invention to the embodiments described herein, will best be understood in conjunction with the accompanying drawings, in which:

FIG. 6b is a dark field transmission electron micrograph of the same area in FIG. 6a;

DETAILED DESCRIPTION OF THE INVENTION

According to the invention, the raw material for obtaining the powder mixture can be $Ca_4(PO_4)_2O$, $CaHPO_4$ $2H_2O$, $CaHPO_4$, $Ca_8H_2(PO_4)_6$ $5H_2O$, $\alpha$-$Ca_3(PO_4)_2$, $\beta$-$Ca_3(PO_4)_2$, $Ca_2P_2O_7$, and $Ca_2H_2P_2O_8$. The powder mixture can be constituted by more than two of the above materials as long as the resulting powder mixture has a molar ratio of Ca to P roughly between 1 and 2. However, the calcium phosphates used in step (a) are preferably $Ca_4(PO_4)_2O$ and $CaHPO_4$ mixed in a molar ratio of 1:1.

Moreover, the powder/solution mixture in step (b) preferably has a concentration of less than 3 g powder mixture per 1 ml of solution.

The powder/solution mixture is preferably heated to a temperature of 50° C.–150° C. in the heating step c.

The process can further include adding approximately 3% by weight of additional phosphate or fluoride-containing compounds to the phosphate ion-containing solution in the step of mixing the apatite crystal-containing powder in a phosphate ion-containing solution. The additional phosphate-containing compounds can be $NaH_2PO_4$ or $NH_4H_2PO_4$ or a mixture thereof; or $CaF_2$, $SrF_2$, $Na_2SiF_6$, $Na_2PO_3F$ or a mixture thereof.

The present invention also provides a fast-setting, bioresorbable calcium phosphate cement prepared by the above described process.

In addition, the present invention provides a composite comprising a fast-setting, bioresorbable calcium phosphate cement prepared by the above described process and at least one other bioresorbable powder, for example calcium phosphate powder or bioresorbable powder is bioactive glass powder.

The following examples are intended to demonstrate the invention more fully without acting as a limitation upon its scope, since numerous modifications and variations will be apparent to those skilled in this art.

PREPARATIVE EXAMPLE 1
Preparation of Conventional CPC Powder

Figure 1:
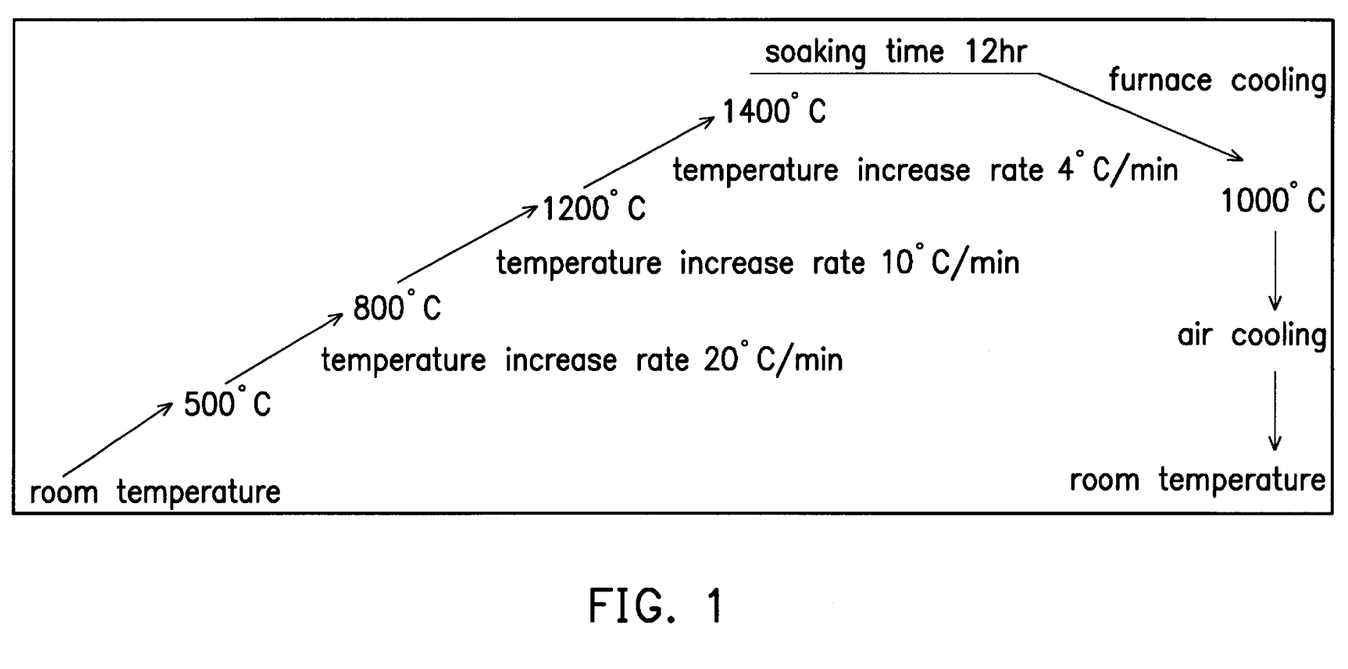
FIG. 1 shows a temperature profile for heating the powder mixture of $Ca_2P_2O_7$ and $CaCO_3$ in the preparation of TTCP powder in preparative example 1.

A $Ca_4(PO_4)_2O$ (TTCP) powder was prepared by mixing $Ca_2P_2O_7$ powder with $CaCO_3$ powder uniformly in ethanol for 24 hours followed by heating to dry. The mixing ratio of $Ca_2P_2O_7$ powder to $CaCO_3$ powder was 1:1.27 (weight ratio) and the powder mixture was heated to react by following the temperature profile as indicated in FIG. 1.

The resulting TTCP powder was then sieved and blended with dried $CaHPO_4$ (DCPA) powder in a ball mill for 12 hours. The blending ratio of the TTCP powder to the DCPA powder was 1:1 (molar ratio) to obtain the conventional CPC powder.

PREPARATIVE EXAMPLE 2
Preparation of Fast-setting, Bioresorbable CPC Powder

A $Ca_4(PO_4)_2O$ (TTCP) powder was prepared by mixing $Ca_2P_2O_7$ powder with $CaCO_3$ powder uniformly in ethanol for 24 hours followed by heating to dry. The mixing ratio of $Ca_2P_2O_7$ powder to $CaCO_3$ powder was 1:1.27 (weight ratio) and the powder mixture was heated to react by following the temperature profile as indicated in FIG. 1.

The resulting TTCP powder was then sieved and blended with dried $CaHPO_4$ (DCPA) powder in a ball mill for 12 hours. The blending ratio of the TTCP powder to the DCPA powder was 1:1 (molar ratio). The resultant powder mixture was added in a 25 mM diluted solution of phosphate to obtain a powder/solution mixture having a concentration of 3 g powder mixture per 1 ml solution. After the powder/solution mixture was dispersed uniformly and formed into pellets, the pellets were heated in an oven at 50° C., 100° C. and 150° C. for 10–45 minutes for drying. The dried pellets were then uniformly ground in a mechanical mill for 15–30 minutes to obtain the fast-setting, bioresorbable calcium phosphate cement powder of the invention.

PREPARATIVE EXAMPLE 3

The conventional CPC powder obtained from preparative Example 1 was added in 0.15 M, 0.3M, 0.5M, 1M and 1.5M solutions of sodium hydrogen phosphate to obtain pastes having a concentration of 4 g powder per 1 ml of solution. The pH of the solution was 7.4. The pastes were uniformly filled in a stainless cylindrical mold having a diameter of 6 mm and a depth of 12 mm. The CPC pastes were then placed in a saturated steam environment for 24 hours to set. The setting times of the CPC pastes are indicated in Table 1 below.

TABLE 1

| Concentration of the sodium hydrogen phosphate | 0.15 M | 0.3 M | 0.5 M | 1 M | 1.5 M |
|---|---|---|---|---|---|
| Setting time | 10 ± 0.87 min | 7.8 ± 0.58 min | 6.7 ± 0.58 min | 3.2 ± 0.29 min | 1.7 ± 0,29 min |

As can be seen from the above Table 1, the setting time of the CPC pastes is shortened from 10 minutes to 1.7 minutes when the concentration of the sodium hydrogen phosphate solutions are increased from 0.15 M to 1.5 M.

Example 1

The CPC powder obtained from preparative Example 1 was added in a 25 mM diluted phosphate solution to obtain a paste having a concentration of 4 g powder per 1 ml solution. The pH value of the paste was tested, 1 minute after the addition, by using a pH meter. 270 seconds after the formation of the paste, the pH was 7. 780 seconds after the formation of the paste, the pH was 7.39, and thereafter remained unchanged.

Figure 2:
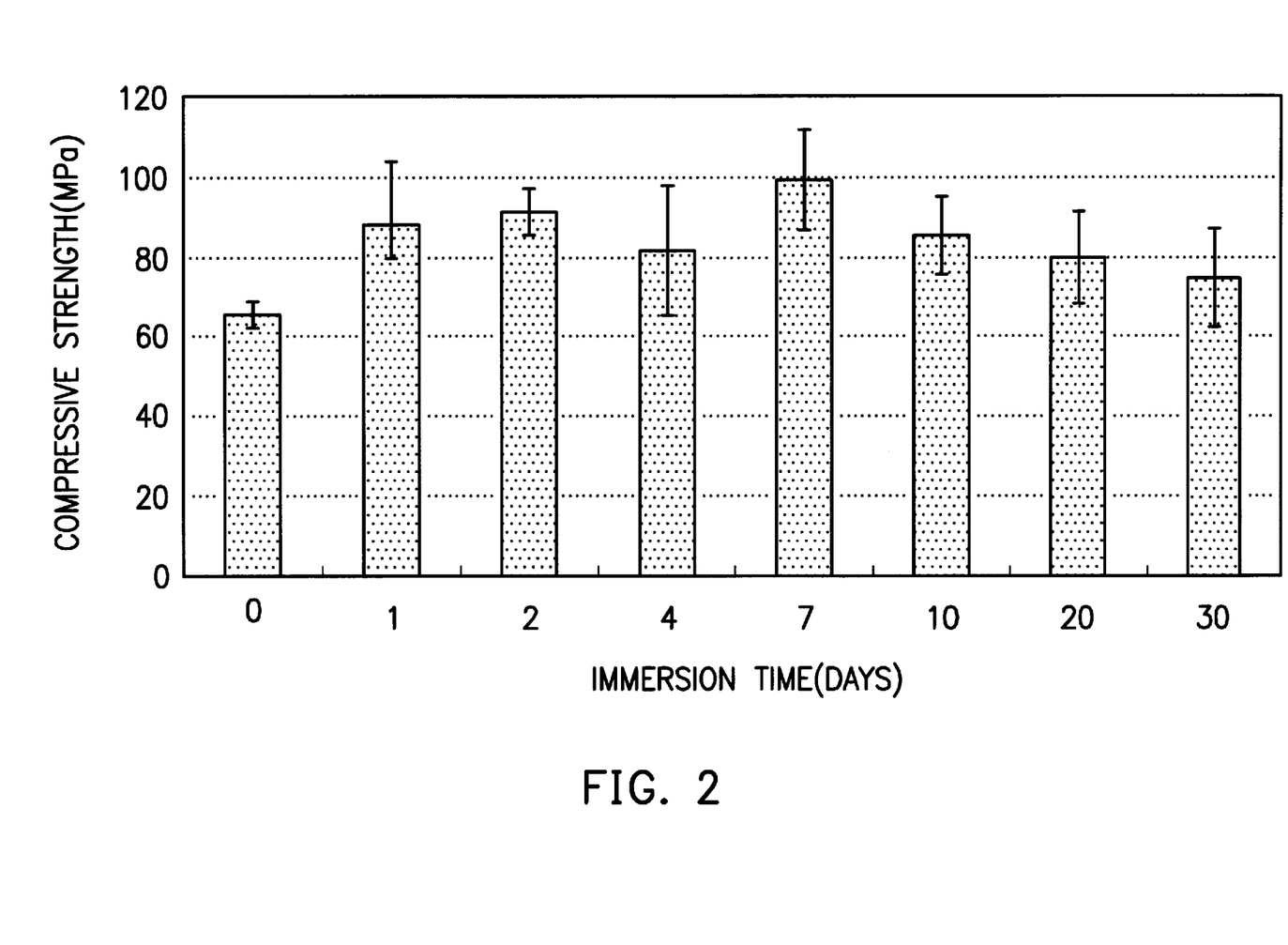
FIG. 2 shows the compressive strengths of the fast-setting, bioresorable CPC specimens after being immersed in Hank's solution for a variable number of days.

The CPC paste was uniformly filled in a stainless cylindrical mold having a diameter of 6 mm and a depth of 12 mm. The CPC paste was then placed in a saturated steam environment for 24 hours to set. The set CPC compressive specimens were then taken out and immersed in Hank's solution for 1,2,4,7,10,20 and 30 days. The compressive strength of the specimens was tested and the results are shown in FIG. 2. As can be seen from FIG. 2, the compressive strength of the specimens is significantly increased from 65.3±3.3 MPa to 87.63±15.83 MPa after being immersed in Hank's solution for only 1 day. And the compressive strength of the specimens is maintained at about 100 MPa after immersing in Hank's solution for more than 7 days, which is much higher than the best compressive strength that can obtained by conventional art. For example, according to Chang Sheng Liu, the best compressive strength of a synthesized CPC is only 51 MPa after being immersed in Hank's solution for 4 hours (Changsheng Liu et al., 1997).

Example 2

Figure 3:
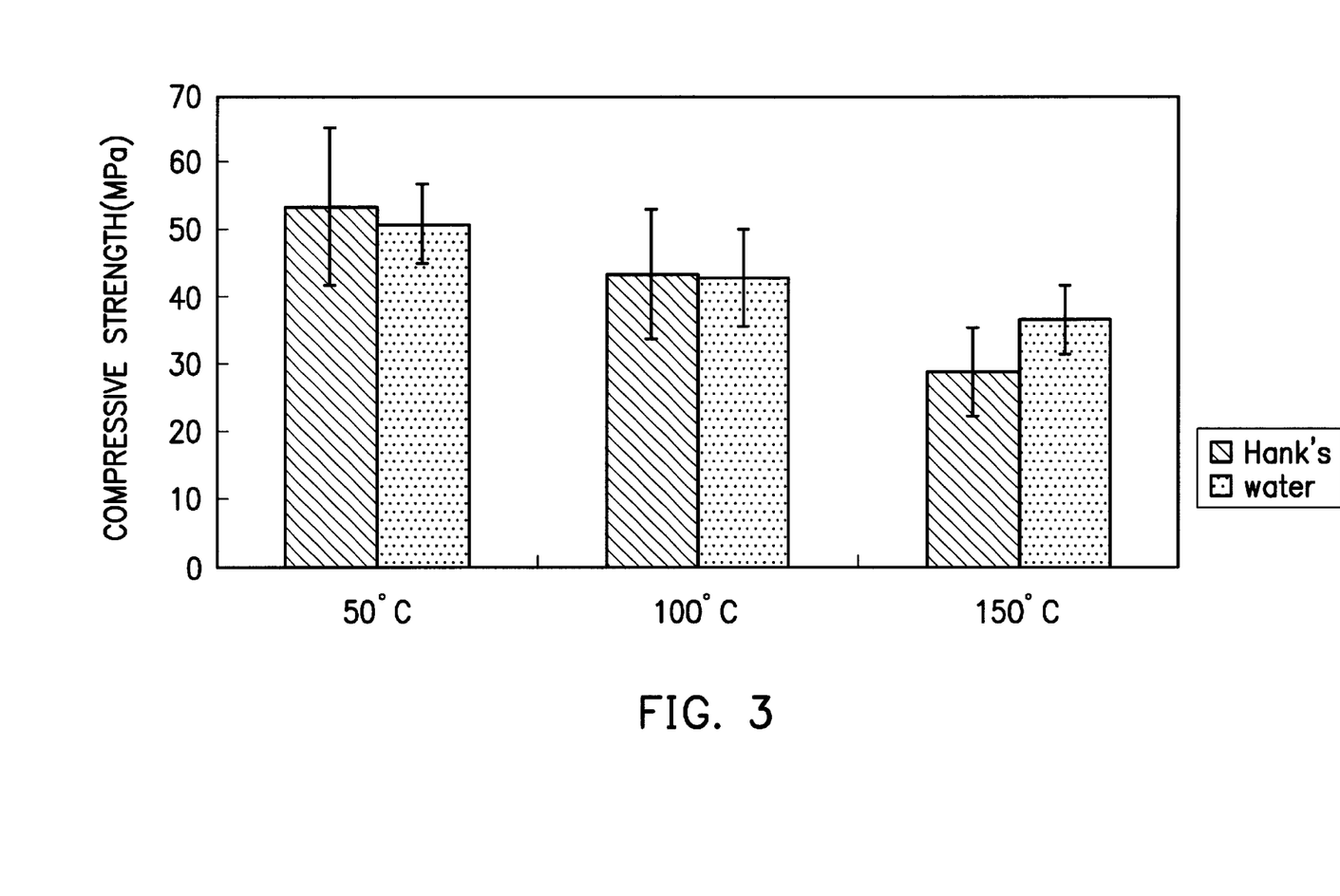
FIG. 3 shows the compressive strengths of the fast-setting, bioresorable CPC specimens obtained from the CPC powder which is heated to a variable temperatures.

The fast-setting, bioresorbable CPC powders obtained from preparative Example 2 were added in 25 mM solution of phosphate to obtain pastes having a concentration of 4 g power per 1 ml of solution. The pastes were then uniformly filled in a stainless cylindrical mold having a diameter of 6 mm and a depth of 12 mm as described in Example 1. The pastes were then allowed to harden in the cylindrical mold for 10 minutes, and soaked in 80 ml of deionized water or Hank's solution. The specimens and the solutions were then together placed in a thermostat at 37° C. for 24 hours. The compressive strength was tested and the results were shown in FIG. 3. As indicated in FIG. 3, the compressive strength of the specimens obtained from the fast-setting, bioresorbable CPC powder which was heated to 50° C., is the highest. However, the compressive strength of the specimens obtained from the fast-setting, bioresorbable CPC powder which was heated to 150° C. is also acceptable for clinical applications.

Example 3

Figure 4:
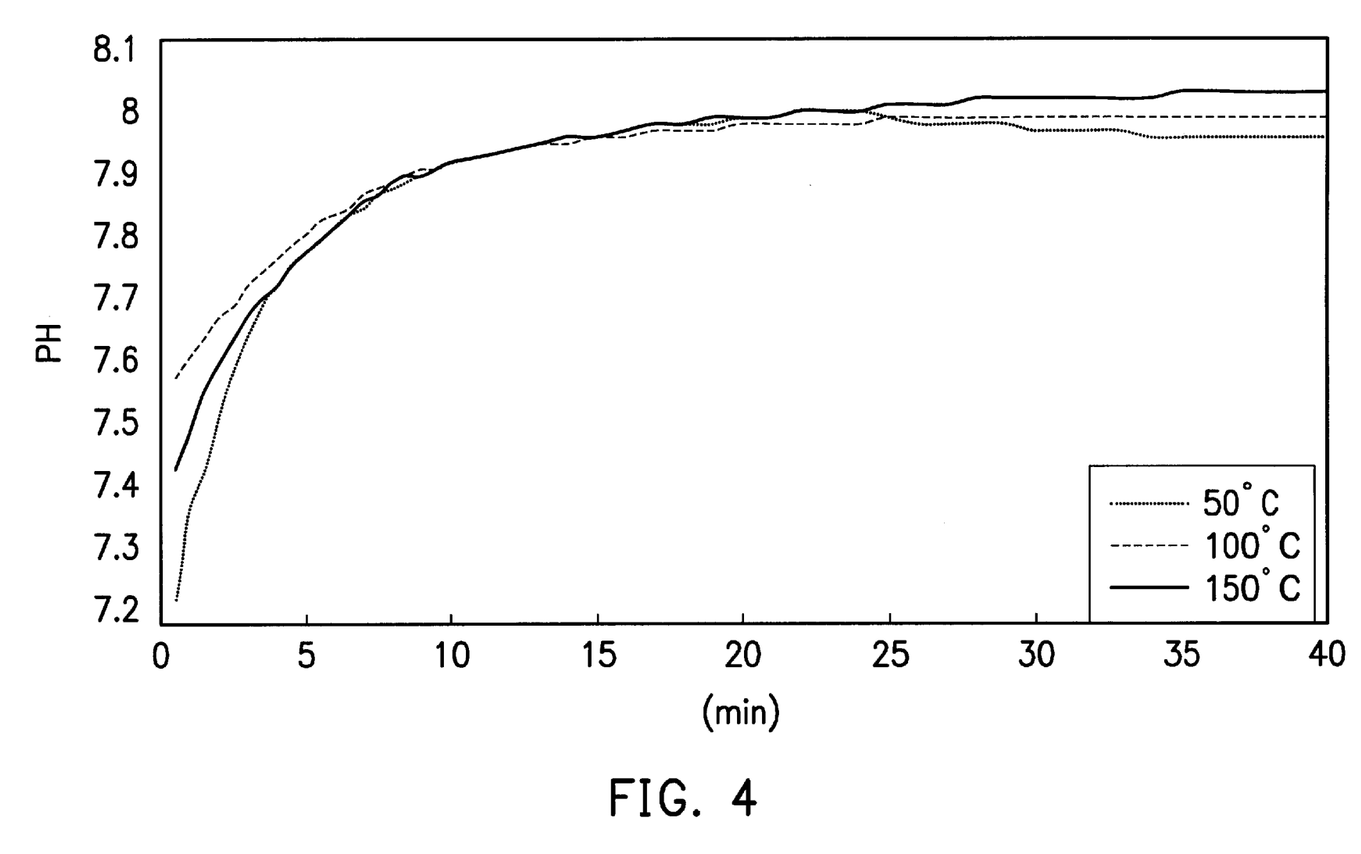
FIG. 4 shows pH values of the fast-setting, bioresorable CPC pastes obtained from the powders which were heated to 50° C., 100° C. and 150° C. in Example 3.

The fast-setting, bioresorbable CPC powders obtained from preparative Example 2 were added in 25 mM solution of phosphate, and mixed for 30 seconds to obtain pastes having a concentration of 4 g power per 1 ml of solution. The pH values of the obtained pastes were then measured by a pH meter and the results are indicated in FIG. 4. As can be seen from the drawing, the pastes obtained from the powders which were heated to 50° C., 100° C. and 150° C. are all near neutral and slightly basic, indicating that the pastes would not irritate living tissues. The working times and the setting times of the pastes were measured and the results are summarized in Table 2 below. The setting time is the time required when a 1 mm diameter pin with a load of 1/4 pounds can be inserted only 1 mm deep into the surface of the paste. The measurement was conducted every 60 seconds after the pastes were formed. The working time is the time after which the paste is too viscous to be stirred. The measurement was conducted every 30 seconds.

TABLE 2

| Temperature | Working time | Setting time |
| --- | --- | --- |
| 50° C. | 6 min 30 sec | 11 min 30 sec |
| 100° C. | 8 min | 11 min 30 sec |
| 150° C. | 8 min 30 sec | 8 min |

Example 4

Figure 5:
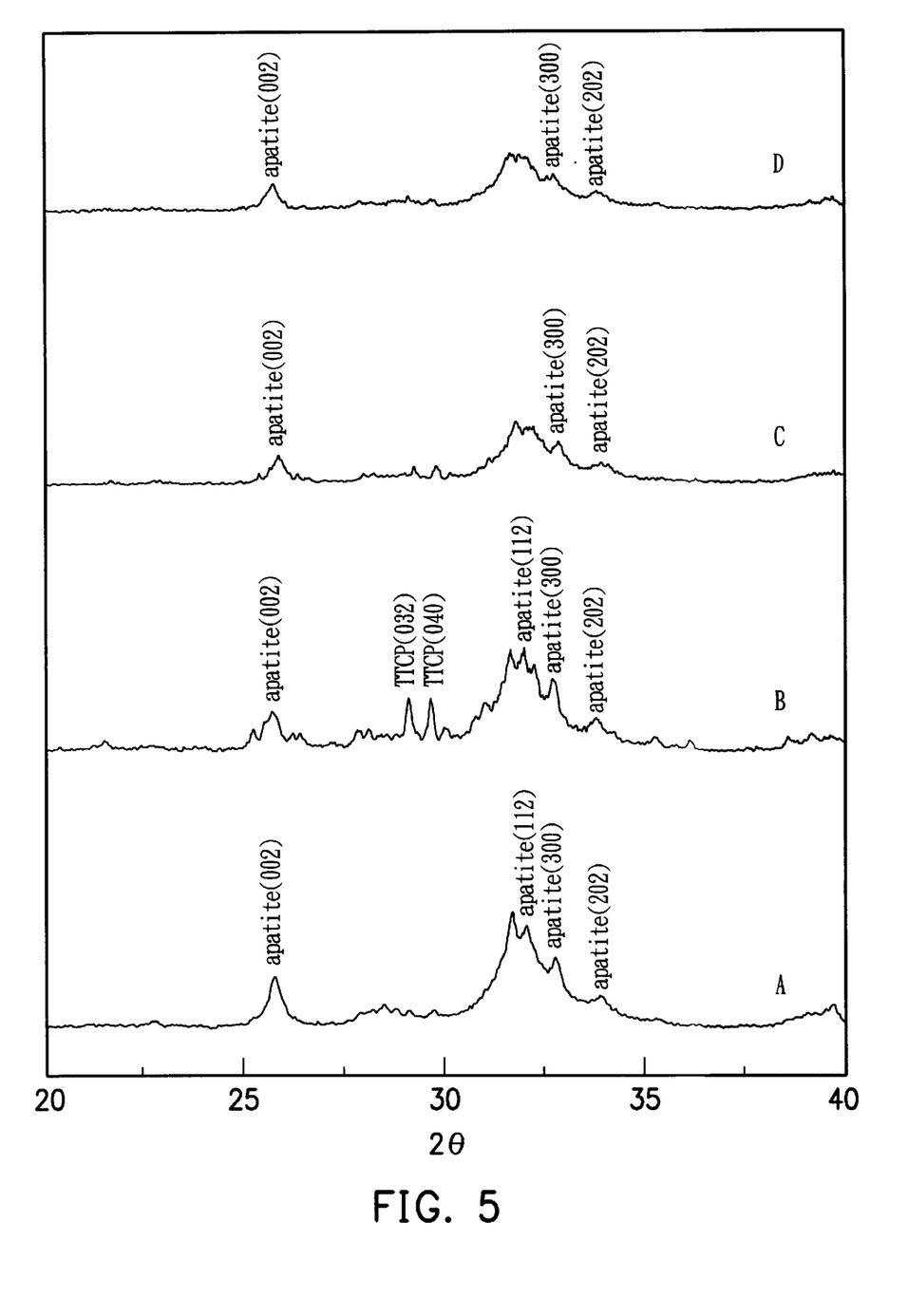
FIG. 5 shows the X-ray diffraction patterns of the conventional CPC specimen, the non-dissolvable, fast-setting CPC specimen and the fast-setting, bioresorbable CPC specimen in Example 4, wherein A represents the X-ray diffraction pattern of the conventional CPC specimen immersed in Hank's solution for 7 days, B represents the X-ray diffraction pattern of the non-dissolvable, fast-setting CPC specimen immersed in Hank's solution for 7 days, C represents the X-ray diffraction pattern of the fast-setting, bioresorbable CPC specimen immersed in Hank's solution for 1 day, and D represents the X-ray diffraction pattern of the fast-setting, bioresorbable CPC specimen immersed in Hank's solution for 7 days.

Specimens prepared from CPC of preparative example 1, fast-setting, non-dissolvable CPC of preparative Example 3 and fast-setting, bioresorable CPC of preparative example 2 were immersed in Hank's solution, and then examined by an X-ray diffractometer. The X-ray diffraction patterns thereof are shown in FIG. 5. As shown in FIG. 5, the crystallinity of the apatite phase decreased with immersion time in the fast-setting, bioresorable CPC.

Example 5

The skull bone of an adult New Zealand white rabbit (weight: 2.8–3.5 kg) was cut from the central portion to reach the periosteum. The periosteum was then peeled off to expose the skull bone. Pastes prepared from fast-setting, non-dissolvable CPC powder and fast-setting, bioresorable CPC powder were then filled in the skull bone via the cuts. The cuts were then sewed up. The skull bone was examined 1 year after the implanting of fast-setting, non-dissolvable CPC paste. It is found that the phase that constitutes the fast-setting, nondissolvable CPC is stable but is not resorbable. However, it is found that only little residual paste remained 6 weeks after the implanting of the fast-setting, bioresorbable CPC paste, and the residual paste was completely absorbed by the bone tissue and disappeared 12 weeks after the implanting of the fast-setting, bioresorbable CPC paste.

Example 6

The inner side of the knee joint of an adult New Zealand white rabbit (weight: 2.8–3.5 kg) was cut to expose the distal epiphysis of the femur. A hole having a diameter of 5 mm was then drilled at the upper portion of the inner ligament. Pastes were prepared from commercially available fillers, Collagraft, high purity $CaSO_4$, the fast-setting, bioresorbable CPC powders obtained from preparative example 2, and composite of the fast-setting, bioresorbable CPC powders. The pastes were fabricated into cylindrical shape by hand and filled in the drilled holes or were injected into the drilled holes by syringe. 12 weeks after the implantation, pictures of the cross sections of the femur in different positions were taken and evaluated. The cross section of the femur in which the drilled hole is empty, i.e. no implant is filled therein was inspected. As no implant material was filled in the drilled hole, the drilled hole was filled with connective tissue, and the connective tissue was detached in an ultrasonic vibration therapy. The picture of the cross section of the femur in which the drilled hole is filled with Collagraft was inspected. The Collagraft material contains abundant crystalline HA and an amount of dissolvable material for inducing the growth of the bone cells. However, as was seen from the picture, although the dissolvable material dissolved after implanting, the crystalline HA remained un-dissolved. The picture of the cross section of the femur in which the drilled hole is filled with high purity commercially available $CaSO_4$ was inspected. As high purity $CaSO_4$ is highly dissolvable, it dissolves so quickly after being implanting in the drilled hole that the bone cells can not grow as quickly as the dissolving rate of the $CaSO_4$. Consequently, as was seen from the picture, the drilled hole is mostly occupied by connective tissue that was easily detached when ultrasonically cleaned. The picture of the cross section of the femur in which the drilled hole is filled with the fabricated cylinder of paste of fast-setting, bioresorbable CPC was inspected. The picture of the cross section of the femur in which the drilled hole is filled with the paste of fast-setting, bioresorbable CPC injected by syringe was inspected. The picture of the cross section of the femur in which the drilled hole is filled with the paste of fast-setting, bioresorbable CPC/α-TCP composite. It is seen from of these photographs that an abundance of the implants have been replaced by new natural bone, indicating the implants of this invention were highly biocompatibe and bioresorbable.

Example 7

Figure 8:
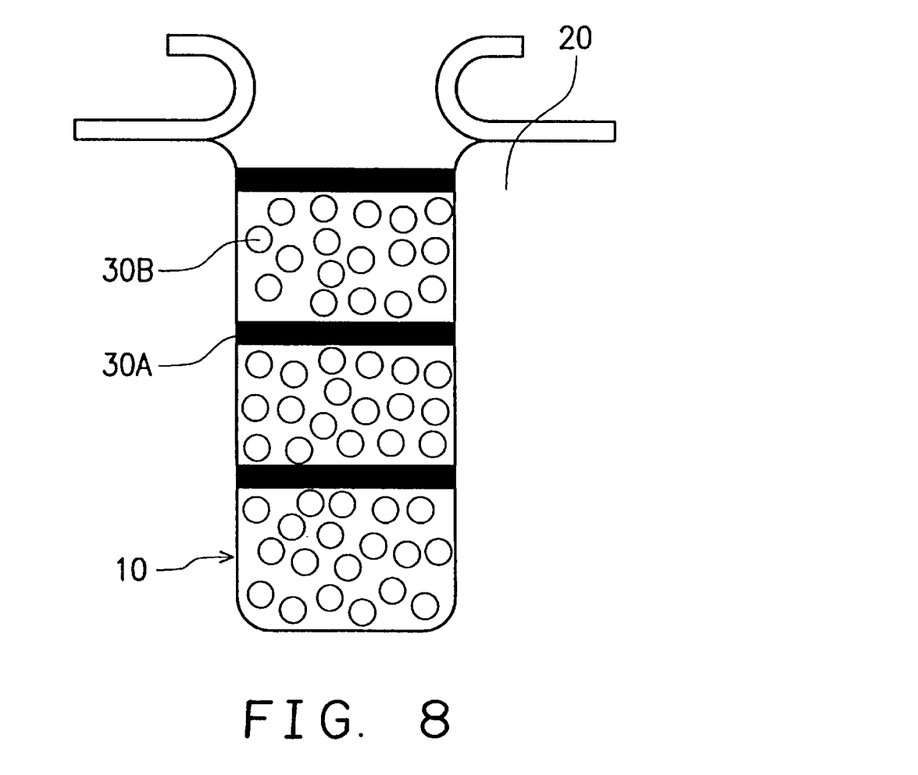
FIG. 8 is a schematic drawing showing an alternative embodiment of a composite consisting of the fast-setting, bioresorbable CPC of the invention and other bioresorbable material being used as the implant of a dental root socket.

The inner side of knee joint of an adult New Zealand white rabbit (weight: 2.8–3.5 kg) was cut to expose the distal epiphysis of the femur. A hole having a diameter of 5 mm was then drilled at the upper portion of the inner ligament. Powders of commercially available fillers, Collagraft, the fast-setting, bioresorbable CPC powders obtained from preparative example 2, and powders of composite of the fast-setting, bioresorbable CPC were then filled in the drilled holes. 12 weeks after the implantation, the light micrographs of the implant-bone interface were taken. It is observed that there is a layer of connective tissue between the implant and the new bone trabeculae and the connective tissue is homogeneously distributed in the periphery of the implanted particles. The connective tissue thus blocks the growth of the osteoblast to form osteoblast depositing osseous tissue. However, as can be seen in FIG. 8*b* and FIG. 8*c,* there is no connective tissue at the interface between the new bone trabeculae and the implant, and several osteoclasts are eroding CPC, indicating the fast-setting, bioresorbable CPC of the invention can be gradually eroded by osteoclasts to form osteoblast depositing osseous tissue. This again verifies that the fast-setting, bioresorbable CPC of the invention has superior osteoconductivity and bioresorbability.

Example 8

Figure 6A:
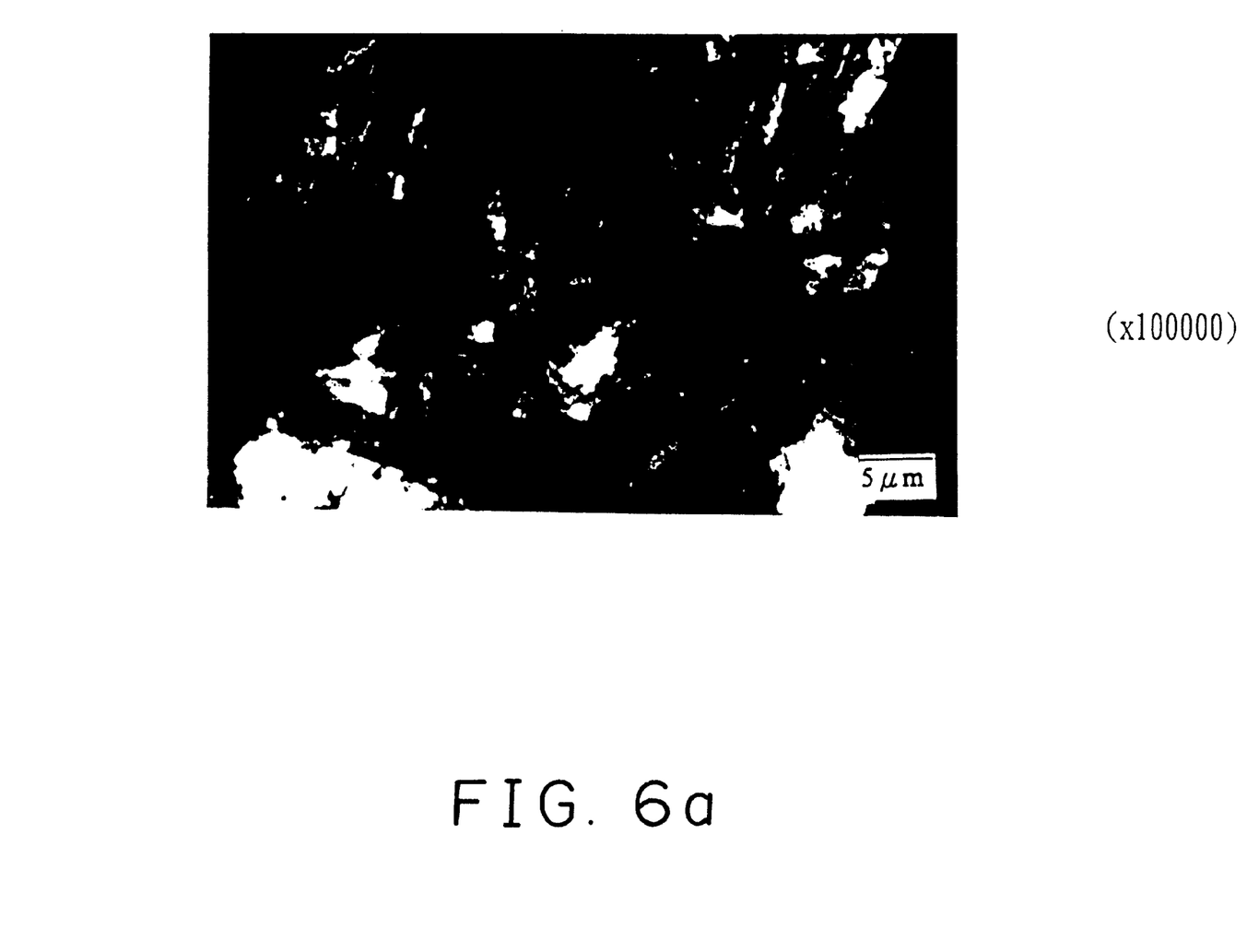
FIG. 6a is a bright field transmission electron micrograph of the fast-setting, bioresorbable CPC powder prepared from the preparative example 2.
Figure 6B:
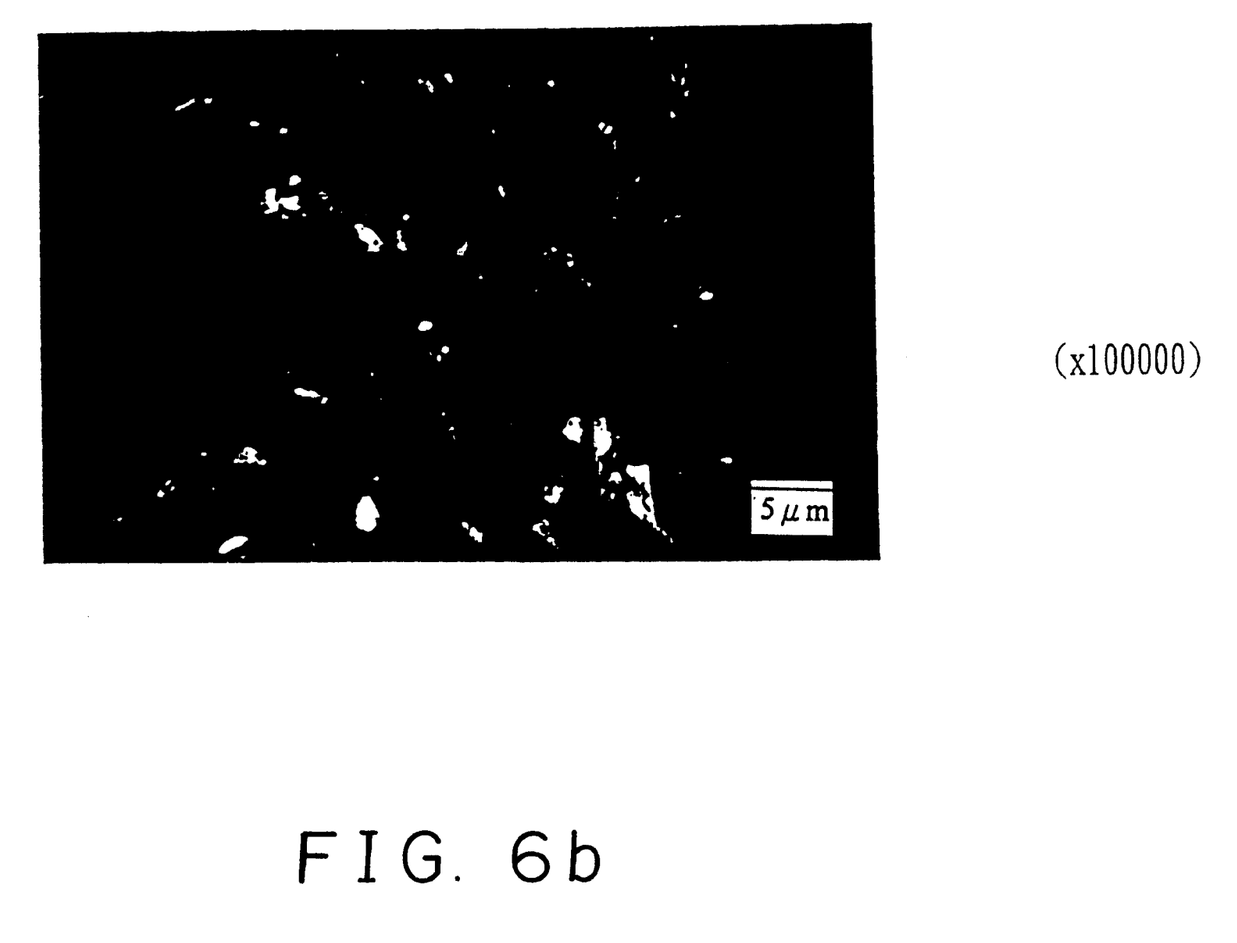
Figure 6C:
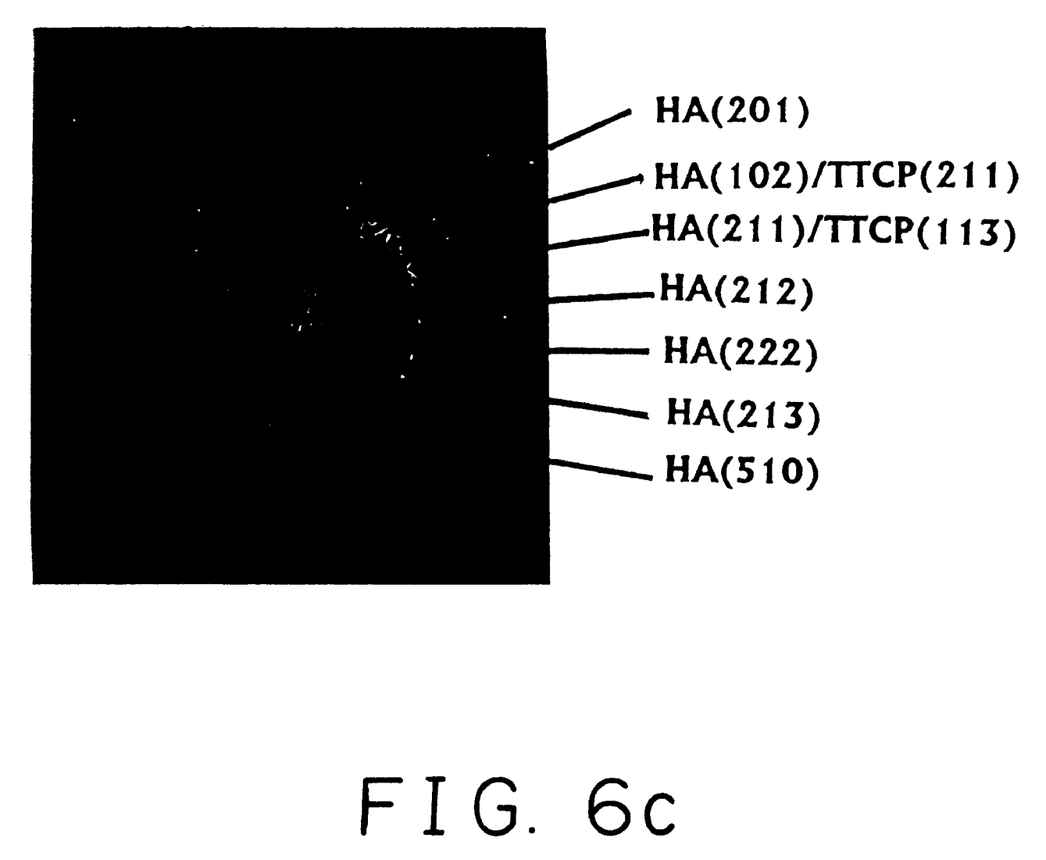
FIG. 6c is a picture showing the selected area electron diffraction pattern of the same area of the same powder prepared from preparative example 2.

The fast-setting, bioresorbable CPC powder prepared from preparative Example 2 was examined by using a transmission electron microscope (TEM). The bright field image, dark field image and the diffraction pattern are respectively shown in FIG. 6*a*, FIG. 6*b* and FIG. 6*c*. It can be seen from the pictures that whisker-like apatite seeds are uniformly distributed in the fast-setting, bioresorbable CPC powder after it is subjected to heat treatment at a temperature of 50° C. The whisker-like phase was confirmed by selected-area electron diffraction analysis as apatite phase. The uniformly distributed submicron-sized apatite whiskers act as reaction seeds to accelerate the fast-setting process of the fast-setting, bioresorbable CPC of the invention.

Example 9

In this example, the influence of the concentration of the powder/solution mixture to the setting time and the compressive strength of the fast-setting, bioresorbable CPC is investigated. Powder/solution mixtures of various concentrations as indicated in Table 3 below were prepared by mixing powder mixture of TTCP and DCPA with 25 mM diluted solution of phosphate. After the powder/solution mixture was dispersed uniformly and formed into pellets, the pellets were heated in an oven at 50° C. for drying. The dried pellets were then uniformly ground in a mechanical mill for 15 minutes to obtain the fast-setting, bioresorbable calcium phosphate cement powders. The powders were added in 25 mM solution of phosphate, and mixed to obtain pastes having various concentrations. The setting times and the working times were measured by the method mentioned previously.

The pastes were also uniformly filled in a stainless cylindrical mold having a diameter of 6 mm and a depth of 12 mm as described in Example 1. The pastes were then allowed to harden in the cylindrical mold for 10 minutes, and soaked in 80 ml of deionized water or Hank's solution. The specimens and the solutions were then placed together in a thermostat at 37° C. for 2, 4 and 24 hours respectively. The specimens were then taken out and their compressive strengths tested. The results of the setting times, the working times and the compressive strengths are summarized below in Table 3.

Example 10

The fast-setting, bioresorbable CPC powders which were dried at 50° C. in Example 9, were added to 25 mM solutions of phosphate. To the solutions of phosphate had been added calcium fluoride ($CaF_2$) to form solutions of 1.0 mM F-ion, 0.5 mM F-ion and 0.25 mM F-ion, respectively. The thus formed pastes had a concentration of 4 g powder in 1 ml of solution. The setting times and the working times of the pastes were measured by the same procedures as in Example 9. Specimens of the pastes were also made and the compressive strength of the specimens were tested by the same procedures as in Example 9. The results are shown below in Table 4.

TABLE 4

| F-ion ratio | 1.0 mM F-ion | 0.5 mM F-ion | 0.25 mM F-ion |
|---|---|---|---|
| Compressive strength | 46.1 ± 8.3 Mpa | 45.8 ± 2.9 Mpa | 32.2 ± 1.0 Mpa |
| Setting time | 10 min 30 sec | 9 min 30 sec | 11 min 30 sec |
| Working time | 8 min | 9 min | 9 min |

As can seen from Table 4, adding fluoride-containing compounds in the phosphate ion-containing solution does not significantly affect the setting time or the working time. However, the compressive strength of the 0.25 mM F-ion specimen was much lower than the 1.0 mM F-ion specimen and the 0.5 mM F-ion specimen.

Figure 7:
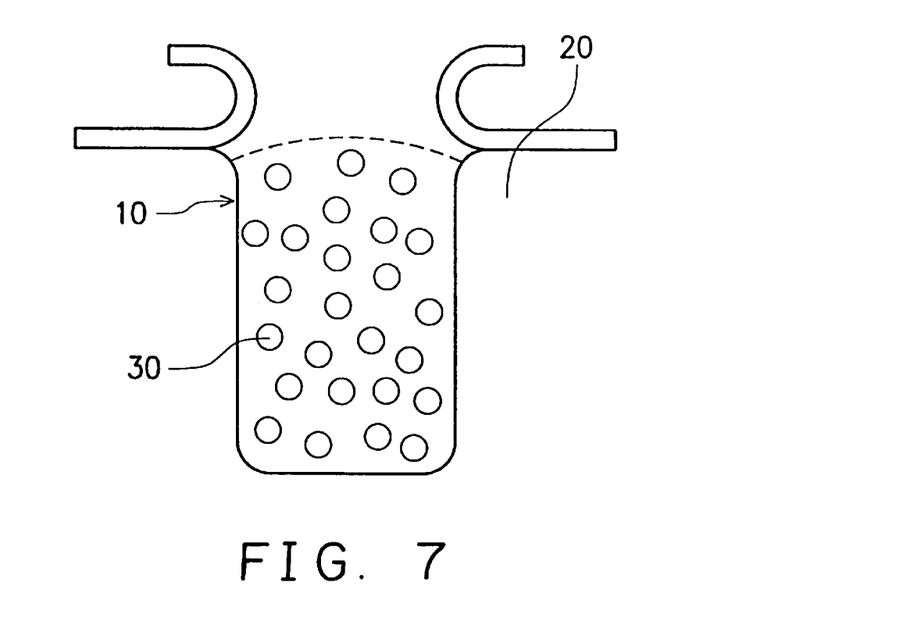
FIG. 7 is schematic drawing showing a composite consisting of the fast-setting, bioresorbable CPC of the invention and other bioresorbable material being used as the implant of a dental root socket.

The calcium phosphate cement of this invention may be employed in a variety of medical and dental procedures to substitute for missing or defective bone or tooth tissue. FIG. 7 illustrates one application of the calcium phosphate cement of this invention to fill in a dental root socket 10 after the extraction of a tooth (not shown). In this embodiment, a composite 30 is composed of a matrix of fast-setting, bioresorbable CPC paste into which a bioresorbable powder, for example calcium phosphate or bioresorbable glass, is

TABLE 3

| Powder/liquid ratio (gm/ml) | Compressive strength (Mpa) 2 hr | Compressive strength (Mpa) 4 hr | Compressive strength (Mpa) 24 hr | Setting time (min) | Working time (min) |
|---|---|---|---|---|---|
| 6 gm/1.92 ml | 24.2 ± 4.0 | 34.8 ± 6.8 | 50.8 ± 5.9 | 11.5 | 6.5 |
| 6 gm/2.4 ml | 8.4 ± 1.2 | 10.2 ± 1.4 | 41.1 ± 3.1 | 6.0 | 5.5 |
| 6 gm/4.8 ml | 11.7 ± 1.4 | 19.1 ± 2.8 | 34.1 ± 8.3 | 6.5 | 5.0 |
| 6 gm/7.2 ml | 8.1 ± 1.6 | 17.4 ± 2.3 | 34.0 ± 12.4 | 5.5 | 4.5 |
| 6 gm/9.6 ml | 4.6 ± 1.7 | 10.2 ± 2.6 | 25.6 ± 3.8 | 6.5 | 4.5 |
| 6 gm/12 ml | 5.6 ± 0.1 | 9.8 ± 1.0 | 22.2 ± 5.2 | 6.0 | 4.5 |
| 6 gm/18 ml | 2.7 ± 0.4 | 6.0 ± 0.3 | 9.6 ± 0.9 | 4.5 | 2.5 |

It can be seen from Table 3 that the lower the powder/liquid ratio, the shorter the setting time and the working time; furthermore, the compressive strength gradually lowers until the powder/liquid ratio is smaller or equal to 0.63. Since the compressive strength of human trabecular bone is 30 MPa, it is desirable that the initial compressive strength, 24 hours after the implantation, can be greater than 30 MPa (Driessens F. C. M. Boltong M. G. Bermudez O., Ginebra M. P>Fernandez E., A new apatite calcium phosphate bone cement:J preliminary results, Bioceramics 6:469–473, 1993); and the setting time can be between 3 minutes and 15 minutes (Khairoun I. Boltong M. G., Driessens F. C. M., Planell J. A., Effect of calcium carbonate on clinical compliance of apatite calcium phosphate bone cement, J. Biomed, Mater. Res., 38:356–360, 1997). In summary, the powder/liquid ratio is preferably greater or equal to 0.83 according to the invention.

interspersed. The composite is filled into socket 10. Upon hardening of the CPC, the socket is securely filled and growth of the bone cells of jawbone 20 is induced.

FIG. 8 illustrates another embodiment of the application of the calcium phosphate cement of this invention to fill in a dental root socket 10. In this embodiment, the socket 10 is filled with alternating layers 30A, composed of the fast-setting, bioresorbable CPC, and layers 30B, composed of a bioresorbable powder, for example calcium phosphate or bioresorbable glass. Upon hardening of the CPC, the socket is securely filled and growth of the bone cells of jawbone 20 is induced.

The use of the fast-setting, bioresorbable calcium phosphate cement of this invention is not limited to filling dental root sockets. Other uses contemplated include (but are not limited to) the uses of any of the cements known in the prior art, for example: (1) cavity bases and liners to protect the pulp, (ii) materials for capping exposed pulps, (iii) materials to replace or promote regeneration of bone mineral lost due to periodontal disease, (iv) direct filling materials that have physical properties similar to enamel and are adhesive to enamel and dentin, (v) a cement to build up alveolar ridges in edentulous patients, (vi) an endodontic filling material for root canals, (vii) a material to cement retention pins, (viii) a self-setting cement for binding non-self-setting calcium phosphate materials such as porous or non-porous HA and .beta.-tricalcium phosphate, (ix) a replacement of bone that has been removed surgically or lost due to trauma, (x) a cement for implanting or replanting teeth, (xi) a luting cement in dentistry and orthopedic surgery, (xii) an investment mold material, (xiii) a material which will promote bone mineral in its vicinity, (xiv) a remineralizing polish for use in place of pumice, and (xv) a root cement for remincralizing and desensitizing of exposed root surfaces, (xvi) a cement for orthopedic prostheses, (xvii) a tooth implant, (xviii) a device for percutaneous passage of tubes, wires and other medical instruments through the skin, and (xix) a replacement material for bone loss due to abscess.

What is claimed is:

1. A process for producing fast-setting, bioresorbable calcium phosphate cements, comprising the following steps:

(a) obtaining a powder mixture from at least one calcium phosphate selected from the group consisting of $Ca_4(PO_4)_2O$, $CaHPO_4 \cdot 2H_2O$, $CaHPO_4$, $Ca_8H_2(PO_4)_6 \cdot 5H_2O$, $\alpha\text{-}Ca_3(PO_4)_2$, $\beta\text{-}Ca_3(PO_4)_2$, $Ca_2P_2O_7$, $Ca_2H_2P_2O_8$, wherein the molar ratio of Ca to P in the mixture is between about 1 and 2;

(b) mixing the powder mixture in a phosphate-containing solution to obtain a powder/solution mixture having a concentration of less than 4 g powder mixture per 1 ml solution;

(c) immediately heating the powder/solution mixture to a temperature of about 50° C.–350° C. to obtain a powder containing uniformly distributed submicron-sized apatite crystals; and (d) mixing the apatite crystal-containing powder in a phosphate ion-containing solution to obtain the fast-setting, bioresorbable calcium phosphate cement.

2. The process as claimed in claim 1, wherein the calcium phosphates used in step (a) are $Ca_4(PO_4)_2O$ and $CaHPO_4$ mixed in a molar ratio of 1:1.

3. The process as claimed in claim 1, wherein the powder/solution mixture in step (b) has a concentration of less than 3 g powder mixture per 1 ml of solution.

4. The process as claimed in claim 1, wherein in step c the aqueous solution is heated to a temperature of 50° C.–150° C.

5. The process as claimed in claim 1, wherein in step (d), approximately 3% by weight of additional phosphate or fluoride-containing compounds are added in the phosphate ion-containing solution.

6. The process as claimed in claim 5, wherein the additional phosphate-containing compounds are selected from the group consisting of $NaH_2PO_4$ and $NH_4H_2PO_4$ and a mixture thereof.

7. The process as claimed in claim 5, wherein the additional fluoride-containing compounds are selected from the group consisting of $CaF_2$, $SrF_2$, $Na_2SiF_6$, $Na_2PO_3F$ and a mixture thereof.

* * * * *

UNITED STATES PATENT AND TRADEMARK OFFICE
CERTIFICATE OF CORRECTION

PATENT NO.    : 6,379,453 B1
DATED         : April 30, 2002
INVENTOR(S)   : Lin et al.

It is certified that error appears in the above-identified patent and that said Letters Patent is hereby corrected as shown below:

<u>Title page,</u>
Item [73], please correct the Assignee's names and addresses as follows:
-- Jiin-Huey Chern Lin, Kaoshiung;
  Chien-Ping Ju, Tainan, both of (TW). --

Signed and Sealed this

Thirty-first Day of December, 2002

JAMES E. ROGAN
*Director of the United States Patent and Trademark Office*